US006201147B1

(12) United States Patent
Bornscheuer et al.

(10) Patent No.: US 6,201,147 B1
(45) Date of Patent: Mar. 13, 2001

(54) PROCESS FOR THE RESOLUTION OF ESTERS OF ARYLALKYLCARBOXYLIC ACIDS

(75) Inventors: Uwe Bornscheuer; Erik Henke, both of Stuttgart (DE); Yang Hong, Canberra (AU)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/399,760

(22) Filed: Sep. 21, 1999

(30) Foreign Application Priority Data

Sep. 30, 1998 (DE) .............................. 198 44 876

(51) Int. Cl.$^7$ .................................................. C07C 69/76
(52) U.S. Cl. .......................................................... 560/103
(58) Field of Search ........................... 558/414; 560/103; 546/112, 268.4; 548/400; 549/13, 29, 356, 429

(56) References Cited

U.S. PATENT DOCUMENTS

| 5,155,028 | 10/1992 | Fülling et al. ...................... 435/117 |
| 5,426,211 | 6/1995 | Fülling et al. ........................ 560/56 |

FOREIGN PATENT DOCUMENTS 0 402 771 B1   12/1990   (EP) .

OTHER PUBLICATIONS

Schoffers et al., *Tetrahedron*, 52(11), 3769–3826, 1996.
Schmid et al., *Angew. Chem. Int. Ed.*, 1998, 37, 1608–1633.
Degueil–Castaing et al., *Tetrahedron Letters*, 28(9), 953–954, 1987.
Wang et al,. *J. Am. Chem. Soc.*, 1988, 110, 7200–7205.
Laumen et al. *J. Chem. Soc., Chem. Commun.*, 1988, 1459–61.
Holmberg et al., *Appl. Microbiol. Biotechnol.*, 1991, 35, 572–578.
Persichetti et al., *Tetrahedron Letters*, 37(36), 6507–6510, 1996.
Ozegowski et al., *Liebigs Ann. Chem.*, 1994, 215–217.
Soumanou et al., *JAOCS*, 75(6), 1998, 703–710.
Bjorkling et al., *J. Chem. Soc., Chem. Commun.*, 1989, 934–935.
McNeill et al., *JAOCS*, 67(11), 1990, 779–783.
Cao et al., *Biocatalysts and Biotransformation*, 14, 269–283, 1997.
Ikeda et al., *Biotechnolog. Bioeng.*, 57, 1998, 624–629.
Sakai et al. *J. Org. Chem.*, 1997, 62, 4906–4907.
Anthosen et al. *Tetrahedron Asymmetry*, 7(9), 2633–2638, 1996.

Primary Examiner—Joseph K. McKane
Assistant Examiner—Joseph Murray
(74) Attorney, Agent, or Firm—Keil & Weinkauf

(57) ABSTRACT

The invention relates to a process for the resolution of esters of arylalkylcarboxylic acids of the general formula

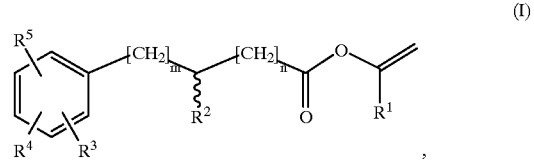
(I)

which comprises reacting compounds of the general formula I with an alcohol of the general formula $R^6$—OH in the presence of a lipase or esterase to give compounds of the general formulae Ia and II

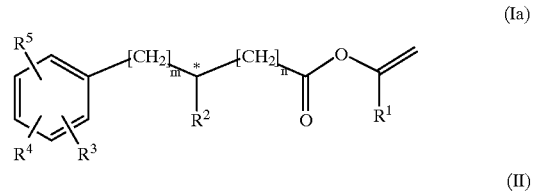
(Ia)

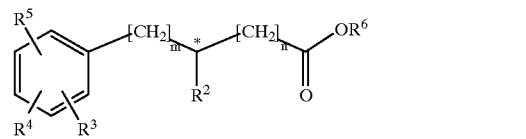

(II)

at least one of the compounds of the formulae Ia and II being present in an enantiomeric excess and the substituents and variables in the formulae I, Ia and II are as defined in the specification.

6 Claims, No Drawings

PROCESS FOR THE RESOLUTION OF ESTERS OF ARYLALKYLCARBOXYLIC ACIDS

The invention relates to a process for the resolution of esters of arylalkylcarboxylic acids.

Lipases and esterases are distinguished by a broad substrate spectrum combined with frequently very high stereoselectivity and stability even in nonaqueous solvents. The successful use of these enzymes is documented in a number of extensive review articles (Schoffers et al., Tetrahedron, 52, 1996: 3769–3826; Kazlauskas & Bornscheuer, Biotransformations, VCH, Weinheim, Vol. 8a, 1998: 37; Schmid et al., Angew. Chem. Int. Ed. Engl., 37, 1998: 1608) and in books (F. Theil, Enzyme in der Organischen Synthese [Enzymes in Organic Synthesis], Spektrum Akademischer Verlag, Heidelberg, 1997; C. H. Wong, G. M. Whitesides, Enzymes in Synthetic Organic Chemistry, Pergamon Press, Oxford, 1994; K. Faber, Biotransformations in Organic Chemistry, A Textbook, 3rd Edition, Springer, Berlin 1997; K. Drauz, H. Waldmann, Enzyme 20 Catalysis in Organic Synthesis, A Comprehensive Handbook, Vol I+II, VCH, Weinheim, 1995).

By means of this enzyme catalysis, optically pure alcohols are readily accessible. To prepare these optically pure alcohols, transesterifications in organic solvents starting from racemic or prostereogenic precursors have been widely described. To increase the reaction rate and to shift the reaction equilibrium, it has proven very useful to employ activated esters, in particular enol esters. Frequently employed acyl donors are vinyl esters and, among these, especially vinyl acetate. The vinyl alcohol formed intermediately in the transesterification is rearranged in a keto-enol tautomerism into the readily volatile acetaldehyde, which leads to a suppression of the undesirable back reaction (see Degueil-Castaing et al., Tetrahedron Lett., 28, 1987: 953–954; Wang et al., J. Am. Chem. Soc., 110, 1988: 7200–7205; Laumen et al., J. Chem. Soc., Chem. Commun., 1988: 1459–1461).

The accessibility in the case of optically active carboxylic acids appears different. Unlike the above-described preparation of optically pure alcohols utilizing the synthesis direction of lipases or esterases in nonaqueous solvents, optically pure carboxylic acids are prepared in the hydrolysis direction, in which the corresponding esters are hydrolyzed. This is necessary, since the enzymes used only accept a very small substrate spectrum in the synthesis direction on the carboxylic acid side and the hydrolysis direction makes possible a wider substrate spectrum. A disadvantage here, however, is that water-labile compounds cannot be used under these conditions. Moreover, a partial or complete racemization of the products can occur in the aqueous medium. This leads to a decrease in the optical purity of the products.

The utilization of the synthesis direction in the preparation of chiral carboxylic acids with nonactivated esters is likewise known from the literature (see Holmberg et al., Appl. Microbiol. Biotechnol., 35, 1992: 572–578; Persichetti et al., Tetrahedron Lett., 37, 1996: 6507–6510; Ozegowski et al., Liebigs Ann. 1994: 215–217). It is affected by further disadvantages, however, in addition to the disadvantage of small substrate breadth already mentioned above. The equilibrium position during resolution in a transesterification reaction with nonactivated esters is very unfavorable and leads either to product mixtures or to very long reaction times. In order to overcome these disadvantages, the reaction for shifting the equilibrium can be carried out in the presence of a molecular sieve (Soumanou et al., J. Am. Oil Chem. Soc., 75, 1998: 703–710), at reduced pressure or with application of a vacuum (Björkling et al., J. Chem. Soc., Chem. Commun., 1989: 934–935) or as a solid-phase synthesis (McNeill et al., J. Am. Oil Chem. Soc., 67, 1990: 779–783; Cao et al., Biocatal. Biotransform., 14, 1997: 269–283), which, however, in each case leads to a technically more complicated reaction.

It is an object of the present invention to develop an access to optically active carboxylic acids, which does not have the abovementioned disadvantages and is easy to carry out.

We have found that this object is achieved by the process according to the invention for the resolution of esters of arylalkylcarboxylic acids of the general formula I

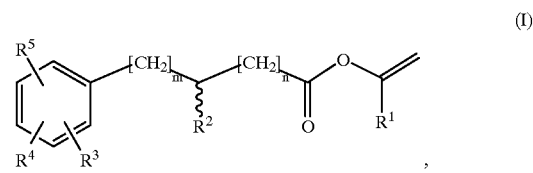

(I)

which comprises reacting compounds of the general formula I with an alcohol of the general formula $R^6$—OH in the presence of a lipase or esterase to give compounds of the general formulae Ia and II

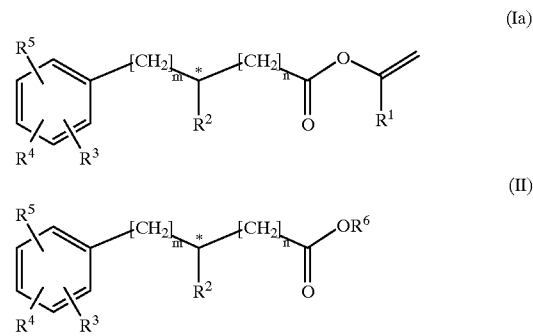

(Ia)

(II)

at least one of the compounds of the formulae Ia and II being present in an enantiomeric excess and the substituents and variables in the formulae I, Ia and II having the following meanings:

*=optically active center n and m independently of one another are 0 or 1

$R^1$=hydrogen or methyl $R^2$=substituted or unsubstituted, branched or unbranched $C_1$–$C_6$-alkyl-, $C_3$–$C_6$-cycloalkyl-, aryl- or hetaryl-, $R^3$, $R^4$, $R^5$ independently of one another are hydrogen, substituted or unsubstituted, branched or unbranched $C_1$–$C_{10}$-alkyl-, $C_2$–$C_{10}$-alkenyl-, $C_2$–$C_{10}$-alkynyl-, $C_1$–$C_{10}$-alkoxy-, $C_2$–$C_{10}$-alkenyloxy-, $C_2$–$C_{10}$-alkynyloxy-, $C_3$–$C_{10}$-cycloalkyl-, $C_3$–$C_{10}$-cycloalkyloxy-, $C_1$–$C_4$-alkylaryl-, $C_1$–$C_4$-alkylhetaryl-, aryl-, hetaryl-, hydroxyl-, halogen-, cyano-, nitro- or amino-, $R^6$=substituted or unsubstituted, branched or unbranched $C_1$–$C_{20}$-alkyl-, $C_1$–$C_{20}$-alkoxy-, $C_2$–$C_{20}$-alkenyl-, $C_3$–$C_{10}$-cycloalkyl- or aryl-, and where two adjacent substituents $R^3$, $R^4$ and $R^5$ together can form a further substituted or unsubstituted aromatic, saturated or partially saturated ring having 5 to 6 atoms in the ring, which can contain one or more heteroatoms such as O, N or S.

$R^2$ in the compounds of the formulae I, Ia and II is substituted or unsubstituted, branched or unbranched $C_1$–$C_6$-alkyl-, $C_3$–$C_6$-cycloalkyl-, aryl- or hetaryl-.

Alkyl radicals which may be mentioned are substituted or unsubstituted branched or unbranched $C_1$–$C_6$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl. Methyl, ethyl, n-propyl, n-butyl, i-propyl and i-butyl are preferred.

Cycloalkyl radicals in the formula which may be mentioned by way of example are substituted or unsubstituted branched or unbranched $C_3$–$C_6$-cycloalkyl chains having 3 to 6 carbon atoms in the ring or ring system, such as cyclopropyl, cyclobutyl, cyclopentyl, cyclohexyl, 1-methylcyclopropyl, 1-ethylcyclopropyl or 1-propylcyclopropyl. The cycloalkyl radicals can also contain heteroatoms such as S, N and O in the ring.

Aryl which may be mentioned is substituted or unsubstituted phenyl or naphthyl. Phenyl and naphthyl are preferred.

Hetaryl radicals which may be mentioned are substituted and unsubstituted hetaryl radicals, which contain one or more nitrogen, sulfur and/or oxygen atoms in the ring or ring system.

Possible substituents of the radicals of $R^2$ mentioned are, for example, one or more substituents such as halogen, such as fluorine, chlorine or bromine, cyano, nitro, amino or hydroxyl. Methyl, chlorine and hydroxyl are preferred.

$R^3$, $R^4$, $R^5$ in the compounds of the formulae I, Ia and II independently of one another are hydrogen, substituted or unsubstituted, branched or unbranched $C_1$–$C_{10}$-alkyl-, $C_2$–$C_{10}$-alkenyl-, $C_2$–$C_{10}$-alkynyl-, $C_1$–$C_{10}$-alkoxy-, $C_2$–$C_{10}$-alkenyloxy-, $C_2$–$C_{10}$-alkynyloxy-, $C_3$–$C_{10}$-cycloalkyl-, $C_3$–$C_{10}$-cycloalkyloxy-, $C_1$–$C_4$-alkylaryl-, $C_1$–$C_4$-alkylhetaryl-, aryl-, hetaryl-, hydroxyl-, halogen- such as fluorine, chlorine or bromine, cyano , nitro or amino . Furthermore, two adjacent substituents $R^3$, $R^4$ and $R^5$ together can form a further substituted or unsubstituted aromatic, saturated or partially saturated ring having 5 to 6 atoms in the ring, which can contain one or more heteroatoms such as O, N or S; such that condensed systems are formed where no more than one ring can be fused to the central ring.

Alkyl radicals which may be mentioned are substituted or unsubstituted branched or unbranched $C_1$–$C_{10}$-alkyl chains such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl or n-decyl. Methyl, ethyl, n-propyl, n-butyl, i-propyl and i-butyl are preferred.

Alkenyl radicals which may be mentioned are substituted or unsubstituted, branched or unbranched $C_2$–$C_{10}$-alkenyl chains, such as, for example, ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl , 6-nonenyl, 7- nonenyl, 8-nonenyl, 1-decenyl, 2-decenyl, 3-decenyl, 4-decenyl, 5-decenyl, 6-decenyl, 7-decenyl, 8-decenyl or 9-decenyl.

Alkynyl radicals which may be mentioned are substituted or unsubstituted, branched or unbranched $C_2$–$C_{10}$-alkynyl chains, such as, for example, ethynyl-, prop-1-yn-1-yl, prop-2-yn-1-yl, n-but-1-yn-1-yl, n-but-1-yn-3-yl, n-but-1-yn-4-yl, n-but-2-yn-1-yl, n-pent-1-yn-1-yl, n-pent-1-yn-3-yl, n-pent-1-yn-4-yl, n-pent-1-yn-5-yl, n-pent-2-yn-1-yl, n-pent-2-yn-4-yl, n-pent-2-yn-5-yl, 3-methylbut-1-yn-3-yl, 3-methylbut-1-yn-4-yl, n-hex-1-yn-1-yl, n-hex-1-yn-3-yl, n-hex-1-yn-4-yl, n-hex-1-yn-5-yl, n-hex-1-yn-6-yl, n-hex-2-yn-1-yl, n-hex-2-yn-4-yl, n-hex-2-yn-5-yl, n-hex-2-yn-6-yl, n-hex-3-yn-1-yl, n-hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl or 4-methylpent-2-yn-5-yl and the higher homologs of this series.

Alkoxy radicals which may be mentioned are substituted or unsubstituted, branched or unbranched $C_1$–$C_{10}$-alkoxy chains such as, for example, methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, hexyloxy, heptyloxy, octyloxy, nonyloxy or decyloxy and their branched-chain homologs.

Alkenyloxy radicals which may be mentioned are substituted or unsubstituted, branched or unbranched $C_2$–$C_{10}$-alkenyloxy chains, such as, for example, ethenyloxy, propenyloxy, 1-butenyloxy, 2-butenyloxy, 3-butenyloxy, 2-methylpropenyloxy, 1-pentenyloxy, 2-pentenyloxy, 3-pentenyloxy, 4-pentenyloxy, 1-methyl-1-butenyloxy, 2-methyl-1-butenyloxy, 3-methyl-1-butenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-1-propenyloxy, 1,2-dimethyl-2-propenyloxy, 1-ethyl-1-propenyloxy, 1-ethyl-2-propenyloxy, 1-hexenyloxy, 2-hexenyloxy, 3-hexenyloxy, 4-hexenyloxy, 5-hexenyloxy, 1-methyl-1-pentenyloxy, 2-methyl-1-pentenyloxy, 3-methyl-1-pentenyloxy, 4-methyl-1-pentenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,1-dimethyl-3-butenyloxy, 1,2-dimethyl-1-butenyloxy, 1,2-dimethyl-2-butenyloxy, 1,2-dimethyl-3-butenyloxy, 1,3-dimethyl-1-butenyloxy, 1,3-dimethyl-2-butenyloxy, 1,3-dimethyl-3-butenyloxy, 2,2-dimethyl-3-butenloxy, 2,3-dimethyl-1-butenyloxy, 2,3-dimethyl-2-butenyloxy, 2,3-dimethyl-3-butenyloxy, 3,3-dimethyl-1-butenyloxy, 3,3-dimethyl-2-butenyloxy, 1-ethyl-1-butenyloxy, 1-ethyl-2-butenyloxy, 1-ethyl-3-butenyloxy, 2-ethyl-1-butenyloxy, 2-ethyl-2-butenyloxy, 2-ethyl-3-butenyloxy, 1,1,2-trimethyl-2-propenyloxy, 1-ethyl-1-methyl-2-propenyloxy, 1-ethyl-2-methyl-1-propenyloxy, 1-ethyl-2-methyl-2-propenyloxy, 1-heptenyloxy, 2-heptenyloxy, 3-heptenyloxy, 4-heptenyloxy, 5-heptenyloxy, 6-heptenyloxy, 1-octenyloxy, 2-octenyloxy, 3-octenyloxy, 4-octenyloxy, 5-octenyloxy, 6-octenyloxy, 7-octenyloxy, 1-nonenyloxy, 2-nonenyloxy, 3-nonenyloxy, 4-nonenyloxy, 5-nonenyloxy, 6-nonenyloxy, 7-nonenyloxy, 8-nonenyloxy, 1-decenyloxy, 2-decenyloxy, 3-decenyloxy, 4-decenyloxy, 5-decenyloxy, 6-decenyloxy, 7-decenyloxy, 8-decenyloxy or 9-decenyloxy.

Alkynyloxy radicals which may be mentioned are substituted or unsubstituted, branched or unbranched $C_2$–$C_{10}$-alkynyloxy chains, such as, for example, ethynyloxy, prop-1-yn-1-yloxy, prop-2-yn-1-yloxy, n-but-1-yn-1-yloxy, n-but-1-yn-3-yloxy, n-but-1-yn-4-yloxy, n-but-2-yn-1-yloxy, n-pent-1-yn-1-yloxy, n-pent-1-yn-3-yloxy, n-pent-1-yn-4-yloxy, n-pent-1-yn-5-yloxy, n-pent-2-yn-1-yloxy, n-pent-2-yn-4-yloxy, n-pent-2-yn-5-yloxy, 3-methylbut-1-yn-3-yloxy, 3-methylbut-1-yn-4-yloxy, n-hex-1-yn-1-yloxy, n-hex-1-yn-3-yloxy, n-hex-1-yn-4-yloxy, n-hex-1-yn-5-yloxy, n-hex-1-yn-6-yloxy, n-hex-2-yn-1-yloxy, n-hex-2-yn-4-yloxy, n-hex-2-yn-5-yl, n-hex-2-yn-6-yloxy, n-hex-3-yn-1-yloxy, n-hex-3-yn-2-yloxy, 3-methylpent-1-yn-1-yloxy, 3-methylpent-1-yn-3-yloxy, 3-methylpent-1-yn-4-yloxy, 3-methylpent-1-yn-5-yloxy, 4-methylpent-1-yn-1-yloxy, 4-methylpent-2-yn-4-yloxy or 4-methylpent-2-yn-5-yloxy and the higher homologs of this series.

Cycloalkyl radicals which may be mentioned by way of example are substituted or unsubstituted branched or unbranched $C_3$–$C_{10}$-cycloalkyl chains having 3 to 7 carbon atoms in the ring or ring system, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl, cyclooctyl, cyclononyl or cyclodecyl. The cycloalkyl radicals can also contain heteroatoms such as S, N and O in the ring.

Cycloalkyloxy radicals which may be mentioned by way of example are substituted or unsubstituted branched or unbranched $C_3$–$C_{10}$-cycloalkyloxy chains having 3 to 7 carbon atoms in the ring or ring system, such as cyclopropyloxy, cyclobutyloxy, cyclopentyloxy, cyclohexyloxy, cycloheptyloxy, 1-methylcyclopropyloxy, 1-ethylcyclopropyloxy, 1-propylcyclopropyloxy, 1-butylcyclopropyloxy, 1-pentylcyclopropyloxy, 1-methyl-1-butylcyclopropyloxy, 1,2-dimethylcyclopropyloxy, 1-methyl-2-ethylcyclopropyloxy, cyclooctyloxy, cyclononyloxy or cyclodecyloxy. The cycloalkyloxy radicals can also contain heteroatoms such as S, N and O in the ring.

$C_1$–$C_4$-alkylaryl which may be mentioned is substituted and unsubstituted branched-chain or unbranched-chain $C_1$–$C_4$-alkylphenyl or $C_1$–$C_4$-alkylnaphthyl radicals such as methylphenyl, ethylphenyl, propylphenyl, 1-methylethylphenyl, butylphenyl, 1-methylpropylphenyl, 2-methylpropylphenyl, 1,1-dimethylethylphenyl, methylnaphthyl, ethylnaphthyl, propylnaphthyl, 1-methylethylnaphthyl, butylnaphthyl, 1-methylpropylnaphthyl, 2-methylpropylnaphthyl or 1,1-dimethylethylnaphthyl.

Alkylhetaryl radicals which may be mentioned are substituted and unsubstituted branched-chain or unbranched-chain $C_1$–$C_4$-alkylhetaryl radicals which contain one or more nitrogen, sulfur and/or oxygen atoms in the ring or ring system.

Aryl is to be understood as meaning, for example, single or fused aromatic ring systems, which can optionally be substituted by one or more radicals such as halogen, such as fluorine, chlorine or bromine, cyano, nitro, amino, hydroxyl, thio, alkyl, alkoxy, aryl, hetaryl or futher saturated or unsaturated nonaromatic rings or ring Systems. Optionally substituted phenyl, methoxyphenyl and naphthyl are preferred.

Hetaryl is to be understood as meaning, for example, single or fused aromatic ring systems-having one or more heteroaromatic 3- to 7-membered rings which can contain one or more heteroatoms, such as N, O or S, and which can optionally be substituted by one or more radicals such as halogen, such as fluorine, chlorine or bromine, cyano, nitro, amino, hydroxyl, thio, alkyl, alkoxy or further aromatic or further saturated or unsaturated nonaromatic rings or ring systems.

Possible substituents of the radicals of $R^3$, $R^4$ and $R^5$ mentioned are in principle all conceivable substituents, for example one or more substituents such as halogen, such as fluorine, chlorine or bromine, cyano, nitro, amino, hydroxyl, alkyl, cycloalkyl, aryl, alkoxy, benzyloxy, phenyl or benzyl.

$R^6$ in the compounds of the formula II is independently substituted or unsubstituted, branched or unbranched $C_1$–$C_{20}$-alkyl-, $C_1$–$C_{20}$-alkoxy-, $C_2$–$C_{20}$-alkenyl-, $C_3$–$C_{10}$-cycloalkyl- or aryl-.

Alkyl radicals which may be mentioned are substituted or unsubstituted, branched or unbranched $C_1$–$C_{20}$-alkyl chains, such as, for example, methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosanyl.

Alkoxy radicals which may be mentioned are substituted or unsubstituted, branched or unbranched $C_1$–$C_{20}$-alkyloxy chains, such as, for example, methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy, 1-ethyl-2-methylpropoxy, hexyloxy, heptyloxy, octyloxy, nonyloxy, decyloxy, undecyloxy, dodecyloxy, tridecyloxy, tetradecyloxy, pentadecyloxy, hexadecyloxy, heptadecyloxy, octadecyloxy, nonadecyloxy or eicosanyloxy.

Alkenyl radicals which may be mentioned are substituted or unsubstituted, branched or unbranched $C_2$–$C_{20}$-alkenyl chains, such as, for example, ethenyl, propenyl, 1-butenyl, 2-butenyl, 3-butenyl, 2-methylpropenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl, 1-heptenyl, 2-heptenyl, 3-heptenyl, 4-heptenyl, 5-heptenyl, 6-heptenyl, 1-octenyl, 2-octenyl, 3-octenyl, 4-octenyl, 5-octenyl, 6-octenyl, 7-octenyl, 1-nonenyl, 2-nonenyl, 3-nonenyl, 4-nonenyl, 5-nonenyl, 6-nonenyl, 7-nonenyl, 8-nonenyl, 1-decenyl, 2-decenyl, 3-decenyl, 4-decenyl, 5-decenyl, 6-decenyl, 7-decenyl, 8-decenyl or 9-decenyl and their higher homologs.

Cycloalkyl radicals which may be mentioned by way of example are substituted or unsubstituted branched or unbranched $C_3$–$C_{10}$-cycloalkyl chains having 3 to 7 carbon atoms in the ring or ring system, such as cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclpropyl, 1-methyl-2-ethylcyclopropyl, cyclooctyl, cyclononyl or cyclodecyl. The cycloalkyl radicals can also contain heteroatoms such as S, N and O in the ring.

Aryl is to be understood as meaning, for example, single or fused aromatic ring systems which can optionally be substituted by one or more radicals such as halogen, such as fluorine, chlorine or bromine, cyano, nitro, amino, hydroxyl, thio, alkyl, alkoxy, aryl, hetaryl or further saturated or unsaturated nonaromatic ring or ring systems. Optionally substituted phenyl, methoxyphenyl and naphthyl are preferred.

The process according to the invention using the vinyl esters or the alkylated vinyl esters (such as isopropenyl esters) leads to an advantageous increase in the reaction rate with a simultaneous considerable increase in the enantioselectivity of the enzymes used (lipases and esterases). Enantiomeric excesses can thus be achieved with high reaction conversions, which are not achievable either in the hydrolysis direction or in transesterification with nonactivated esters. At about 40% conversion, enantiomeric purities for the substrate of at least 60% ee, preferably at least 70% ee, are achieved. The enantiomeric purities for the product are advantageously at least 30% ee, preferably 50% ee. The reaction rates can be increased by at least 10-fold compared with the nonactivated esters, preferably by at least 20-fold, particularly preferably by at least 30-fold. The reaction in, for example, phosphate buffer is markedly higher, but the selectivity is unacceptable. Under the conditions according to the invention, enantioselectivities (=E) of at least E=20 up to E>100 can be achieved (for calculation see examples).

The process according to the invention is advantageously carried out in the presence of at least one further organic solvent, but can also be carried out without the presence of further solvents. In this case, the alcohol used for the transesterification ($R^6$—OH) serves as a solvent. Alcohols which can be used in principle are all primary and secondary alcohols. Secondary alcohols, however, exhibit a lower activity in the reaction, tertiary alcohols can also be used in principle. The reaction times with these alcohols, however, are unsatisfactory. Examples of advantageous alcohols which may be mentioned are primary aliphatic branched or unbranched alcohols such as methanol, ethanol, propanol, butanol, pentanol, hexanol, heptanol, nonanol or decanol. Secondary alcohols which may be mentioned are aliphatic alcohols such as i-propanol or i-butanol. Cyclic aliphatic alcohols or aromatic alcohols can also be used. Methanol, ethanol, isopropanol and hexanol are preferably used.

Possible additional solvents are all organic solvents which can increase the starting material solubility and product solubility and thus positively affect the reaction time. Aprotic solvents such as toluene, hexane or benzene or polar aprotic solvents such as DMSO, DMF or N-methylpyrrolidone are advantageously used for the process according to the invention.

The process according to the invention can be carried out at temperatures between −50° C. and +100° C. When using thermostable enzymes, even higher conversion temperatures can be achieved (see, for example Ikeda et al, Molecular cloning of extremely thermostable esterase gene from hyperthermophilic archaean Pyrococcus furiosus in Escherichia coli, Biotechnol. Bioeng., 57, 1998: 624–629). In the range from 0° C. or below, the reaction rate markedly decreases. A reaction in this range, however, is possible in principle as can be inferred from Sakai et al. (Enhancement of the enantioselectivity in lipase-catalysed kinetic resolutions of 3-phenyl-2H-azirine-2-methanol by lowering the temperature to −40 degrees, J. Org. Chem., 62, 1997: 4906–4907). The process is preferably carried out between 0° C. and 90° C., particularly preferably between 10° C. and 80° C.

In principle, all lipases or esterases such as microbial, animal or plant lipases or esterases are suitable for the process according to the invention. Bacterial or fungal lipases or esterases or porcine pancreatic lipase are/is advantageously used. Lipases are preferably used. Suitable lipases are bacterial or fungal lipases which have been isolated from the genera Arthrobacter, Alcaligenes, Bacillus, Brevibacterium, Pseudomonas, Chromobacterium, Aspergillus, Candida, Fusarium, Geotrichum, Humicola, Mucor, Pichia oder Rhizopus. The reaction can also be carried out in the presence of the complete organisms or crude extracts of the organisms. Advantageously suitable are lipases from the genera and species Arthrobacter sp., Alcaligenes sp., Bacillus cereus, Bacillus subtilis, Bacillus coagulans, Brevibacterium ammoniagenes, Pseudomonas aeruginosa, Pseudomonas cepacia, Pseudomonas fluorescens, Pseudomonas sp., Chromobacterium viscosum, Aspergillus niger, Candida antartica, Candida cylindracea, Candida rugosa, Fusarium solani, Geotrichum candidum, Humicola lanuginosa, Mucor javonicus, Mucor mihei, Mucor sp., Pichia miso, Rhizopus nigricans, Rhizopus oryzae or Rhizopus sp. Commercially obtainable lipases or formulations of these lipases, which are obtainable, for example, from the companies Amano, Novo or Boehringer Mannheim, are also suitable for the process according to the invention. The lipases from Candida antartica, which are obtainable in two isoforms A or B or a mixture thereof, or lipases from Candida cylindracea are preferred. These enzymes are suitable for the process according to the invention as free enzymes or as enzyme formulations, for example as the lipase Chirazyme L2 from the Company Boehringer Mannheim or as Novozym 435 from the Company Novo. Candida antartica Lipase B (=CAL-B) is particularly preferred.

Advantageously, the process according to the invention is carried out in a combination of primary alcohol with an aprotic solvent, such as the combination of n-hexanol and toluene. The starting material (=racemic vinyl ester or racemic alkylated vinyl ester) is introduced into the alcohol or into the solvent/alcohol mixture. The reaction is started by addition of the ensyme. By way of example, Scheme I shows a corresponding reaction. The products formed are the vinyl ester, the hexyl ester and the aldehyde or the ketone not shown in Scheme I. At least one of the reaction products vinyl ester (=substrate) or hexyl ester (=product, see above) show an enantiomeric excess in the reaction. Enantiomeric purities such as described above are preferably achieved.

Scheme I:
Transesterification with vinyl esters (= 1) and alkylated vinyl esters (= 2)

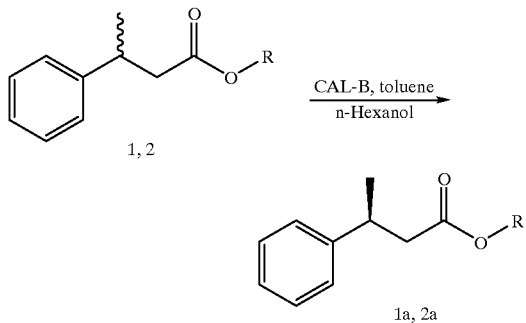

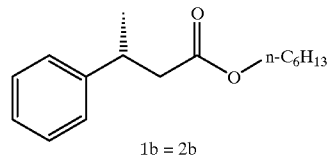

1: R = CH=CH$_2$; 2: R = C(CH$_3$)=CH$_3$

Using the process according to the invention, optically active carboxylic acids can advantageously be prepared rapidly in good yields (>40% yield) and high enantiomeric purities (at least 60% ee).

EXAMPLES

If not described otherwise, the $^1$H-NMR spectra were recorded at 250.1 and 500.1 MHz and the $^{13}$C-NMR spectra at 62.9 and 125.7 MHz in CDCl$_3$ using tetramethylsilane as an internal standard. In cases in which both the racemate and the enatiomeric pure compounds were synthesized, the racemate was used for the full characterization of the compound. Chemical and optical purity of the compounds were demonstrated or determined by means of NMR and GC analysis in comparison to the racemate. The gas-chromatography (=GC) analyses were carried out with an Optima 5 column (25 m×0.25 mm; Macherey & Nagel, Duren, Germany) for the determination of the conversion and purity and with a heptakis-(2,3-di-O-acetyl-6-O-TBDMS) -β-cyclodextrin column (25 m×0.25 mm, Prof. W. A. König, University of Hamburg, Germany) for the determination of the enantiomeric excess. The immobilized lipase used was Candida antarctica lipase (Chirazyme L-2, c.-f., C2, 5000 U/g) from Boehringer Mannheim, Penzberg, Germany, if not described otherwise. The absolute configuration of the biotransformation products was determined by means of comparison with optically pure standards, which were prepared from the commercially obtainable optically pure carboxylic acids. The enantiomeric excess was calculated by comparison with literature values. The enantioselectivity was determined using the formula $E=[\ln\{(1-c)\times(1-ee_s)\}]/[\ln\{(1-c)\times(1+ee_s)\}]$, Preparation of the vinyl esters and analyses The vinyl esters were prepared according to the method described by Wang et al. (J. Am. Chem. soc., 110, 1988: 7200). 500 mg of the carboxylic acids and HgOAc$_2$ (70 mg, 0.22 mmol) were dissolved in 10 ml of vinyl acetate. The solution was stirred at room temperature (=about 23° C.) for 30 min, then 0.1 ml of conc. H$_2$SO$_4$ was added. The solution was refluxed for 6 hours and cooled to room temperature. 400 mg of NaOAc were then added to quench the catalyst. The solution was filtered and concentrated. The crude products were then purified by means of silica gel chromatography (petroleum ether:Et$_2$O, 20:1). All vinyl esters were obtained as colorless liquids which needed no further purification. Optically pure vinyl esters were synthesized in smaller amounts using from 60–120 mg of optically pure carboxylic acids.

Vinyl (±)-2-phenylbutyrate (±)-3: The preparation was carried out according to the method described above using 500 mg (=3.05 mmol) of the corresponding carboxylic acid [2-phenylbutyric acid=(±)-12]. 290 mg of (±)-3 (1.52 mmol, 50%) were obtained. Analytical result: C, 75.80; H, 7.41.; calc. for C$_{12}$H$_{14}$O$_2$: C, 75.76; H, 7.42; $^1$H NMR (500.1 MHz; CDCl$_3$) δ 0.91 (t, J=7.4, 3 H), 1.80–2.16 (m, 2 H), 3.51 (t, J=7.7, 1 H), 4.54 (dd, J=6.32, 1.6, 1 H), 4.85 (dd, J=14.0, 1.7, 1 H), 7.23–7.34 (m, 6 H); $^{13}$C NMR (125.8

MHz; CDCl₃) δ 12.08, 26.62, 53.17, 97.90, 127.41, 128.00, 128.67, 138.28, 141.32, 171.12, IR (KBr)/cm⁻¹: 3080 w, 3050 w, 3015 w, 2955 vs, 2920 s, 2860 w, 1750 vs, 1640 vs, 1595 w, 1475 s, 1447 s, 1130 br, 860 s, 720 s, 680 vs.

Vinyl R-(−)-2-phenylbutyrate R-(−)-3: 120 μl of R-(−)-12 (126.6 mg, 0.77 mmol) afforded 44 mg of R-(−)-3 (0.23 mmol, 30%); $[\alpha]_D^{22}$=−23.9° (c=0.664, CHCl₃).

Vinyl (±)-2-phenylpropionate (±)-4: 420 μl of (±)-13 (460.7 mg, 3.07 mmol) afforded 210 mg of (±)-4 (1.19 mmol, 39%): Analytical result: C, 74.73; H, 6.93; calc. for C₁₁H₁₂O₂; C, 74.98; H, 6.86; ¹H NMR (500.1 MHz; CDCl₃) 1.53 (d, J=7.2, 3 H), 3.79 (q, J=7.1, 1 H), 4.54 (d, J=6.18; 1 H), 4.77 (d, J=14.0, 1 H), 7.23–7.35 (m, 6 H); ¹³C NMR (125.7 MHz; CDCl₃) 18.41, 45.26, 97.92, 127.36, 127.52, 128,73, 139.71, 141.36, 171.59; IR (KBr)/cm⁻¹: 3080 w, 3050 w, 3020 s, 2970 s, 2920 s, 2860 w, 1750 vs, 1640 vs, 1595 w, 1485 s, 1445 s, 1140 br, 860 s, 715 s, 680 vs.

Vinyl R-(−)-2-phenylpropionate R-(−)-4: 60 μl of R-(−)-13 (65.8 mg, 0.44 mmol) afforded 18 mg of R-(−)-4 (0.10 mmol, 23%) $[\alpha]_D^{22}$=−34.60 (c=0.900, EtOH).

Vinyl (±)-3-phenylbutyrate (±)-5: 500 mg of (±)-14 (3.05 mmol) afforded 300 mg of (±)-5 (1.58 mmol, 52%): Analytical result: C, 75.63; H, 7.68; calc. for C₁₂H₁₄O₂: C, 75.76; H, 7.42; ¹H NMR (250.1 MHz; CDCl₃) δ 1.25 (d, J=7.0, 3 H), 2.59 (m, 2 H), 3.24 (m, 1 H), 4.47 (dd, J=6.3, 1.5, 1 H), 4.77 (dd, J=14.0, 1.5, 1 H), 7.13–7.27 (m, 6 H); ¹³C NMR (62.9 MHz; CDCl₃) δ 21.82, 36.27, 42.60, 97.76, 126.63, 126.78, 128.66, 141.18, 145.41, 169.48; IR (KBr)/cm⁻¹: 3070 w, 3050 w, 3010 s, 2950 s, 2910 w, 2860 w, 1750 vs, 1640 vs, 1595 w, 1485 s, 1445 s, 1140 br, 860 s, 745 s, 680 vs.

Vinyl R-(−)-3-phenylbutyrate R-(−)-5: 120 μl of R-(−)-14 (128.3 mg, 0.78 mmol) afforded 29 mg of R-(−)-5 (0.15 mmol, 19%) $[\alpha]_D^{22}$=−21.20 (c=1.543, 1,4-dioxane).

Preparation of the ethyl esters and analyses

To prepare the ethyl esters, the corresponding carboxylic acids were dissolved with stirring in a mixture of EtOH (=ethanol, 15 ml) and toluene (100 ml) in a 250 ml two-necked flask with a reflux condenser and Dean-Stark trap. 0.5 ml of conc. H₂SO₄ was then added. The reaction mixture was heated under reflux until water no longer separated (about 6 hours). After cooling to room temperature (about 23° C.), the reaction mixture was washed with 100 ml of ice water, 100 ml of saturated sodium hydrogen-carbonate solution and again with 100 ml of ice water in a separating funnel. The organic phase was dried over sodium sulfate, filtered and the product was purified by means of silica gel chromatography (petroleum ether:ether, 15:1). The ethyl esters were isolated as a colorless liquid (3.1 g, 53%). Optically pure ethyl esters were synthesized in smaller amounts using 60–120 mg of carboxylic acid.

Ethyl (±)-2-phenylbutyrate (±)-6: Preparation was carried out by the method described above using 5.0 g (=30.5 mmol) of the corresponding carboxylic acid [2-phenylbutyric acid=(±) -12]. 3.1 g of (±)-6 (16.1 mmol, 53%) were obtained as a colorless oil. Analytical result: C, 74.96; H, 8.54; calc. for C₁₂H₁₆O₂; C, 74.97; H, 8.39; ¹H NMR (250.1 MHz; CDCl₃) δ 0.82 (t, J=7.4, 3 H), 1.13 (t, J=7.1, 3 H), 1.66–2.08 (m, 2 H), 3.36 (t, J=7.7, 1 H), 4.04 (m, 2 H), 7.23 (m, 5 H), ¹³C NMR (62.9 MHz; CDCl₃) δ 12.24, 14.22, 26.88, 53.63, 60.66, 127.16, 128.02, 128.58, 139.34, 174.14; IR (KBr)/cm⁻¹: 3070 w, 3050 w, 3015 s, 2970 vs, 2920 s, 2880 w, 2860 w, 1735 vs, 1595 w, 1580 s, 1450 vs, 1160 br, 740 s, 680 s.

Ethyl R-(−)-2-phenylbutyrate R-(−)-6: 120 μl of R-(−)-12 (126.6 mg, 0.77 mmol) afforded 80 mg of R-(−)-6 (0.42 mmol, 55%); $[\alpha]_D^{22}$=−65.7° (c=1.508, Et₂O).

Ethyl (±)-2-phenylpropionate (±)-7: 2.0 g of (±)-13 (13.3 mmol) afforded 1.1 g of (±)-7 (6.2 mmol, 47%) as a colorless oil: Analytical result: C, 74.08; H, 8.01; calc. for C₁₁H₁₄O₂: C, 74.13; H, 7.92; ¹H NMR (250.1 MHz; CDCl₃) δ 1.21 (t, J=7.1, 3 H), 1.51 (d, J=7.2, 3 H), 3.72 (q, J=7.2, 1 H), 4.13 (m, 2 H), 7.23–7.34 (m, 5 H); ¹³C NMR (62.9 MHz; CDCl₃; Me₄Si) δ 14.19, 18.68, 45.64, 60.79, 127.13, 127.54, 128.65, 140.78, 174.63; IR (KBr)/cm⁻¹: 3070 w, 3050 w, 3015 s, 2970 vs, 2920 vs, 2880 w, 2860 w, 1760 vs, 1595 w, 1445 s, 1160 br, 840 s, 750 s, 720 s, 680 s.

Ethyl R-(−)-2-phenylpropionate R-(−)-7: 60 μl of R-(−)-13 (65.8 mg, 0.44 mmol) afforded 38 mg of R-(−)-7 (0.21 mmol, 48%); $[\alpha]_D^{22}$=−60.0° (c=1.630, CHCl₃).

Ethyl (±) -3-phenylbutyrate (±)-8: 5.0 g of (±) -14 (30.5 mmol) afforded 3.1 g of (±) -8 (16.1 mmol, 53%) as a colorless oil: Analytical result: C, 74.89; H, 8.52; calc. for C₁₂H₁₆O₂: C, 74.97; H, 8.39; ¹H NMR (250.1 MHz; CDCl₃) δ 1.19 (t, J=7.1; 3 H), 1.32 (d, J=7.0, 3 H), 2.58 (m, 2 H), 3.30 (m, 1 H), 4.09 (q, J=7.1, 2 H), 7.17–7.36 (m, 5 H) ; ¹³C NMR (62.9 MHz; CDCl₃) δ 14.24, 21.88, 36.60, 43.08, 60.31, 126.45, 126.84, 128.54, 145,83, 172.46; IR (KBr)/cm⁻¹: 3070 w, 3050 w, 3020 w, 2960 vs, 2920 s, 2860 w, 1735 vs, 1595 w, 1445 s, 1160 br, 740 s, 680 s.

Ethyl S-(+)-3-phenylbutyrate S-(+)-8: 120 μl of S-(+)-14 (128.3 mg, 0.78 mmol) afforded 60 mg of S-(+)-8 (0.31 mmol, 40%); $[\alpha]_D^{22}$=21.40 (c=1.538, Et₂OH).

Preparation of the hexyl esters and analyses

To prepare the hexyl esters, the corresponding carboxylic acids were dissolved in a mixture of n-hexanol (3.5 ml) and toluene (50 ml) in a round-bottomed flask together with toluene-4-sulfonic acid (20 mg). The flask was provided with a reflux condenser and a Dean-Stark trap before the solution was refluxed. The reaction was carried out until water no longer separated. The mixture was then washed with ice water (30 ml), saturated Na₂CO₃ solution (30 ml) and again with water (30 ml). After drying over Na₂SO₄ and stripping of the solvent, the product was purified by means of silica gel chromatography (petroluem ether: Et₂O, 40:1). A colorless oil was obtained.

Hexyl (±)-2-phenylbutyrate (±)-9: Preparation was carried out by the method described above using 500 mg (=3.05 mmol) of the corresponding carboxylic acid [2-phenylbutyric acid=(±)-12]. 510 mg of (±) -9 (2.05 mmol, 67%) were obtained. Analytical result: C, 77.54; H, 9.78.; calc. for C₁₆H₂₄O₂: C, 77.38; H, 9.74; ¹H NMR (250.1 MHz; CDCl₃) δ 0.76–0.85 (m, 6 H), 1.17 (m, 6 H), 1.49 (t, J=6.7, 2 H), 1.66–2.09 (m, 2 H), 3.36 (t, J=7.7, 1 H), 3.98 (dt, J=6.6, 1.8, 2 H), 7.16–7.25 (m, 5 H); ¹³C NMR (62.9 MHz; CDCl₃) δ 12.25, 14.02, 22.53, 25.52, 26.73, 28.59, 31.40, 53.70, 64.82, 127.15, 128.02, 128.56, 139.36, 141.32, 174.20; IR (KBr)/cm⁻¹: 3070 w, 3050 w, 3015 w, 2950 vs, 2920 vs, 2860 s, 2840 s, 1730 vs, 1595 w, 1485 s, 1447 s, 1160, 890 w, 750 w, 720 s, 680 vs.

Hexyl R-(−)-2-phenylbutyrate R-(−)-9: 120 μl of R-(−)-12 (126.6 mg, 0.77 mmol) afforded 61 mg of R-(−)-9 (0.25 mmol, 32%); $[\alpha]_D^{22}$=−29.30 (c=1.438, CHCl₃).

Hexyl (±)-2-phenylpropionate (±)-10: 100 μl of (±)-13 (109.7 mg, 0.73 mmol) afforded 91 mg of (±)-10 (0.39 mmol, 53%): Analytical result: C, 76.93; H, 9.56; calc. for C₁₅H₂₂O₂: C, 76.88; H, 9.46; ¹H NMR (250.1 MHz; CDCl₃) δ 0.78 (t, J=6.6, 3 H) , 1.14–1.22 (m, 6 H); 1.42 (d, J=7.2, 3 H), 1.48 (t, J=6.8, 2 H) (q, J=7.2, 1 H); 3.97 (t, J=6.7, 2 H), 7.15–7.25 (m, 5 H); ¹³C NMR (62.9 MHz; CDCl₃) δ 14.00, 21.88, 22.52, 25.54, 28.55, 31.41, 36.56, 43.01, 64.50, 126.37, 126.75, 128.47, 145.75, 172.60; IR (Kbr)/cm⁻¹: 3075 w, 3050 w, 3015 w, 2940 vs, 2920 vs, 2860 s, 2840 s, 1735 vs, 1595 w, 1485 vs, 1445 vs, 1160 vs, 890 w, 750 w, 710 w, 680 vs.

Hexyl R-(−)-2-phenylpropionate R-(−)-10: 60 μl of R-(−)-12 (65.8 mg, 0.44 mmol) afforded 39 mg of R-(−)-10 (0.17 mmol, 39%); $[\alpha]_D^{22}$=−35.80 (c=1.580, CHCl$_3$).

Hexyl (±)-3-phenylbutyrate (±)-11: 130 mg of (±)-14 (0.79 mmol) afforded 98 mg (±)-11 (0.39 mmol, 49%): Analytical result: C, 77.42; H, 9.80; calc. for $C_{16}H_{24}O_2$: C, 77.38; H, 9.74; $^1$H NMR (250.1 MHz; CDCl$_3$) δ 0.81 (t, J=6.7, 3 H), 1.18–1.26 (m, 9 H), 1.46 (t, J=6.8, 2 H), 2.51 (m, 2 H), 5.80 (m, 1 H), 3.93 (t, J=6.7, 2 H), 7.11–7.25 (m, 5 H); $^{13}$C NMR (62.9 MHz; CDCl$_3$) δ 14.00, 21.88, 22.52, 25.54, 28.55, 31.41, 36.56, 43.01, 64.50, 126.37, 126.75, 128.47, 145.75, 172.50; IR (KBr)/cm$^{-1}$: 3070 w, 3050 w, 3015 w, 2950 vs, 2920 vs, 2860 s, 2840 s, 1740 vs, 1595 w, 1485 s, 1445 vs, 1160 vs, 890 w, 745 s, 710 s, 680 vs.

Hexyl R-(−)-3-phenylbutyrate R-(−)-11: 120 μl of R-(−)-14 (128.3 mg, 0.78 mmol) afforded 78 mg of R-(−)-11 (0.31 mmol, 40%); $[\alpha]_D^{22}$=−21.6° (c=2.730, CHCl$_3$).

Lipase-catalyzed transesterification: 100 μl of the vinyl esters (0.52 mmol) and 560 μl of n-hexanol (4.49 mmol) were dissolved in 5 ml of toluene in a 10 ml round-bottomed flask and the reaction mixture was mixed at 40° C. or 60° C. on a thermostatted magnetic stirrer. The reaction was started by addition of 100 mg of CAL-B lipase (500 U) (see Scheme II). Samples were taken from the reaction, diluted with toluene and the lipase was removed by means of centrifugation. The samples were analyzed by GC using the Optima 5 column. After ending the reaction by filtration, product and unreacted substrate were purified by flash chromatography. The enantiomeric purities were determined by means of the specific rotation. In the case of the substrates (±)-3, (±)-4 and (±)-6, the optical purity was additionally determined by means of chiral GC. The ethyl esters were correspondingly reacted as a comparison experiment (see Scheme III). The hydrolysis of the ethyl esters was carried out as a further comparison experiment (see Scheme III).

Hydrolysis of the ethyl esters

The hydrolysis of the ethyl esters was carried out with pH-statting. In general, 1 mmol of substrate (6–8) was taken up at 40° C. in 20 ml of phosphate buffer (50 mM, pH 7.5). 200 mg of CAL-B (1000 U) were added at the start of the reaction. The pH was kept constant through the reaction using 0.1 N NaOH. After consumption of base indicated a marked conversion of the substrate, unused substrate was removed by means of extraction with heptane. The aqueous supernatant was then saturated with NaCl and the pH was adjusted to pH 3 using H$_2$SO$_4$ and the mixture was then extracted 3 times with EtOAc in order to obtain the free carboxylic acid (12–14). The organic phases were dried using Na$_2$SO$_4$ and the enantiomeric excess was determined for all compounds by means of the specific rotation and for (±)-6 additionally by means of chiral GC.

The results of these transesterification and hydrolysis experiments can be seen from Table I.

Scheme II:
Resolution of vinyl esters

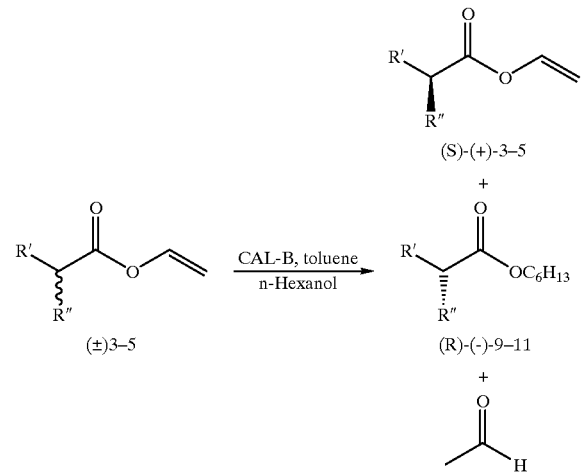

3: R' = Ph, R" = CH$_2$CH$_3$,
4: R' = Ph, R" = CH$_3$
5: R' = H, R" = CH(Ph)CH$_3$

Scheme III:
Resolution of the ethyl esters by
transesterification or hydrolysis

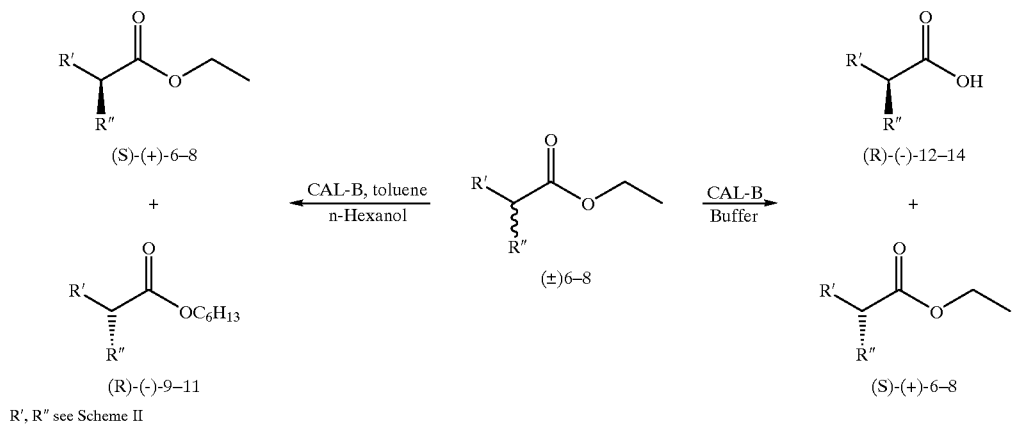

R', R" see Scheme II

TABLE I

Results of the transesterification with vinyl esters or ethyl esters and of the hydrolysis with ethyl esters

| Compound | Reaction time[a] (h) | Yield (%) | Enantiomeric excess (% ee$_s$)[c] | (% ee$_p$)[d] | E[b] |
|---|---|---|---|---|---|
| (±)-3 | 68 | 43 | 74(3) | 99(9) | >100 |
| (±)-6 | 304 | 18 | 14(6) | 66(9) | 5.7 (110)[e] |
| (±)-6 | 1 | 43 | 34(6) | 22(12) | 3.7 |
| (±)-4 | 1.3 | 47 | 75(4) | 53(10) | 26 |
| (±)-7 | 44 | 44 | 41(7) | 68(10) | 6.8 (123)[e] |
| (±)-7 | 0.3 | 47 | 38(7) | 28(13) | 3.5 |
| (±)-5 | 68 | 56 | 86(5) | 31(11) | 13 (23[f]) |
| (±)-8 | 720 | 19 | 22(8) | 60(11) | 4.9 (135)[e] |
| (±)-8 | 3 | 56 | 93(8) | 13(14) | 9 |

[a]Reaction at 40° C.
[b]Calculated according to Chen et al., J. Am. Chem. Soc., 104, 1982: 7294
[c]All unreacted substrate had the S configuration
[d]All prepared product had the R configuration
[e]The values in brackets correspond to the equilibrium constants calculated according to Anthonsen et al., Tetrahedron Asymmetry 7, 1996: 2633
[f]at room temperature (about. 23° C.)

Preparation of ibuprofen vinyl ester and analyses
Chemical synthesis of ibuprofen vinyl ester 1 g (4.85 mmol) of ibuprofen, 171 mg (0.76 mmol) of palladium(II) acetate and 27 mg (0.48 mmol) of potassium hydroxide were dissolved in 48 ml (44.7 g, 0.52 mol) of vinyl acetate. The solution was refluxed for 18 hours. The reaction solution was then filtered off from the solid, the vinyl acetate was distilled off and the remaining crude product was purified by flash chromatography on silica gel (developer: ligroin/diethyl ether 20:1). Yield: 0.92 g (3.96 mmol, 82%).

Lipase-catalyzed transesterification with methanol

The racemic ibuprofen vinyl ester (209 mg, 0.90 mmol) and methanol (240 mg, 7.5 mmol) were disolved in 8 ml toluene and stirred at 40° C. The reaction was started by adding 416 mg of lipase CAL-B (L-2, c.f., C2, lyo.; Boehringer Mannheim). After 5 hours, the reaction was completed by filtering off the lipase, and the reaction mixture was analyzed by gas chromatography in a chiral column (2,3 di-O-methyl-6-O-pentyl-ε-cyclodextrin). The product and unreacted substrate were purified by flash chromatography on silica gel (developer: ligroin/diethyl ether 35:1). Conversion (GC): 40.5%; Yields: ibuprofen methyl ester 64 mg (0.29 mmol; 32%), ee$_p$=76% (GC); ibuprofen vinyl ester 98 mg (0.42 mmol, 47%), ee$_s$=52% (calculated from conversion and ee$_p$). An E value of 12 is calculated from conversion and ee$_p$.

Ibuprofen methyl ester: $^1$HF-NR (250.1 MHz, CDCl$_3$), δ [ppm]: 0.82 (d, 6 H, J=6.6 p2); 1.41 Hz (d, 3 H, J=7.2 Hz); 1.77 (septet, 1 H, J=6.8); 2.37 (d, 2 H , J=7.2 Hz); 3.58 (s, 3 H); 3.70 (q, 1 H, J=7.2 Hz); 7.00–7.18 (m, 4 H). $^{13}$C-NMR (62.9 MHz, CDCl$_3$), δ [ppm]: 18.70; 22.47; 30.25; 45.10; 45.11; 52.05; 127.20; 129.43; 137.82; 140.63; 175.30

Ibuprofen vinyl ester: $^1$H-R (250.1 mz, CDCl$_3$), δ [ppm]: 0.90 (d, 6 H, J=6.6 Hz); 1.52 Hz (d, 3 H, J=7.1 Hz); 1.85 (septet, 1 H, J=6.7); 2.45 (d, 2 H , J=7.2 Hz); 3.75 (q, 1 H, J=7.2 Hz); 4.55 (dd, 1 H, J=1.6, J=6.3); 4.86 (dd, 1 H, J=1.6, J=14.0); 7.00–7. 18 (m, 4 H). $^{13}$C-NMR (62.9 MHz, CDCl$_3$), δ [ppm]: 18.50; 22.46; 30.25; 44.96; 45.11; 97.92; 127.27; 129.51; 136.97; 140.89; 141.50; 171.90

We claim:

1. A process for the resolution of esters of arylalkylcarboxylic acids of the general formula I

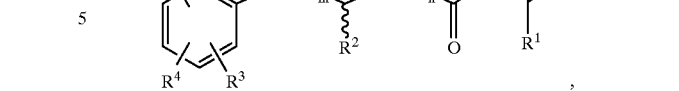
(I)

which comprises reacting compounds of the general formula I with an alcohol of the general formula R$^6$-OH in the presence of a lipase or esterase to give compounds of the general formulae Ia and II

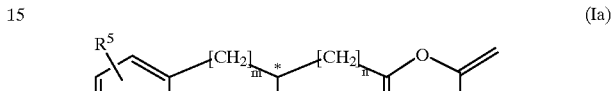
(Ia)

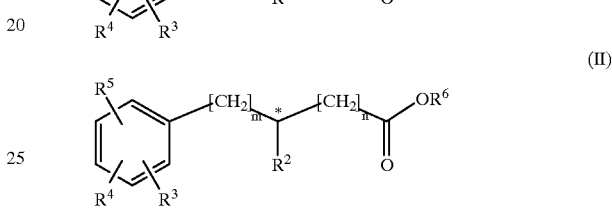
(II)

at least one of the compounds of the formulae Ia and II being present in an enantiomeric excess and the substituents and variables in the formulae I, Ia and II having the following meanings:

*=optically active center n and m independently of one another are 0 or 1

R$^1$=hydrogen or methyl

R$^2$=substituted or unsubstituted, branched or unbranched C$_1$–C$_6$-alkyl-, C$_3$–C$_6$-cycloalkyl-, aryl- or hetaryl-, R$^3$, R$^4$, R$^5$ independently of one another are hydrogen, substituted or unsubstituted, branched or unbranched C$_1$–C$_{10}$-alkyl-, C$_2$–C$_{10}$-alkenyl-, C$_2$–C$_{10}$-alkynyl-, C$_3$–C$_{10}$-cycloalkyl-, C$_3$–C$_{10}$-cycloalkyloxy-, C$_1$–C$_4$-alkylaryl-, C$_1$–C$_4$-alkylhetaryl-, aryl-, hetaryl-, hydroxyl-, halogen-, cyano-, nitro- or amino-, R$^6$=substituted or unsubstituted, branched or unbranched C$_1$–C$_{20}$-alkyl-, C$_1$–C$_{20}$-alkoxy-, C$_2$–C$_{20}$-alkenyl-, C$_3$–C$_{10}$-cycloalkyl- or aryl-, and where two adjacent substituents R$^3$, R$^4$ and R$^5$ together can form a further substituted or unsubstituted aromatic, saturated or partially saturated ring having 5 to 6 atoms in X the ring, which can contain one or more heteroatoms selected from O, N or S.

2. A process as claimed in claim 1, wherein the resolution is carried out in the presence of an organic solvent.

3. A process as claimed in claim 1, wherein the resolution is carried out at temperatures between –50° C. and +100° C.

4. A process as claimed in claim 1 wherein bacterial or fungal lipases or porcine pancreatic lipase are/is used.

5. A process as claimed in claim 1 wherein a bacterial or fungal lipase of the genera Arthrobacter, Bacillus, Brevibacterium, Pseudomonas, Chromobacterium, Aspergillus, Candida, Fusarium, Geotrichum, Humicola, Mucor, Pichia or Rhizopus is used.

6. A process as claimed in claim 1 wherein the lipase used is Candida antarctica lipase.

* * * * *

UNITED STATES PATENT AND TRADEMARK OFFICE
CERTIFICATE OF CORRECTION

PATENT NO. : 6,201,147 B1  Page 1 of 1
DATED : March 13, 2001
INVENTOR(S) : Bornscheuer et al.

It is certified that error appears in the above-identified patent and that said Letters Patent is hereby corrected as shown below:

<u>Column 16,</u>
Line 50, delete "X".

Signed and Sealed this

Fourteenth Day of August, 2001

*Attest:*

*Attesting Officer*

NICHOLAS P. GODICI
*Acting Director of the United States Patent and Trademark Office*